(12) United States Patent
Bachur, Jr. et al.

(10) Patent No.: US 8,815,574 B2
(45) Date of Patent: Aug. 26, 2014

(54) DETECTION METHOD AND APPARATUS FOR DETECTING MICROBIAL GROWTH

(75) Inventors: Nicholas R. Bachur, Jr., Monkton, MD (US); John W. Neubert, Westminster, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1176 days.

(21) Appl. No.: 11/315,612

(22) Filed: Dec. 22, 2005

(65) Prior Publication Data

US 2006/0160171 A1 Jul. 20, 2006

Related U.S. Application Data

(60) Provisional application No. 60/639,366, filed on Dec. 27, 2004.

(51) Int. Cl.
| | |
|---|---|
| *C12M 1/34* | (2006.01) |
| *C12M 3/00* | (2006.01) |
| *B01L 7/00* | (2006.01) |
| *C12M 1/42* | (2006.01) |
| *C12N 13/00* | (2006.01) |

(52) U.S. Cl.
CPC *B01L 7/52* (2013.01); *C12M 35/02* (2013.01); *C12N 13/00* (2013.01)
USPC ........ 435/287.2; 435/40; 435/285.2; 435/450

(58) Field of Classification Search
CPC ............ C12Q 1/04; C12Q 1/045; C12Q 1/10; C12Q 1/18; C12Q 1/34; C12Q 1/686; C12Q 1/6844; C12Q 1/689; C12Q 1/6853; C12Q 1/6848; F04B 19/006; B01L 2300/0816; B01L 200/0415; B01L 3/50273; B01L 7/52; B01L 2300/0636; G01N 27/44704; B01J 2219/00722; B01J 2219/00659; C40B 40/06
USPC ............ 435/40, 285.2, 450, 34, 285.3, 287.1
See application file for complete search history.

(56) References Cited

U.S. PATENT DOCUMENTS

| | | | | |
|---|---|---|---|---|
| 4,250,266 A | * | 2/1981 | Wade | 422/64 |
| 4,321,545 A | * | 3/1982 | Cameron | 324/442 |
| 4,603,581 A | * | 8/1986 | Yamanoue et al. | 73/304 C |
| 5,182,193 A | | 1/1993 | Mishima et al. | |
| 5,465,619 A | * | 11/1995 | Sotack et al. | 73/304 C |

(Continued)

FOREIGN PATENT DOCUMENTS

| | | |
|---|---|---|
| EP | 0277789 A3 | 8/1988 |
| GB | 2260407 | 4/1993 |

(Continued)

OTHER PUBLICATIONS

PCT Search Report for PCT/US2005/046873, Mailed on Apr. 20, 2006.

(Continued)

*Primary Examiner* — Michael Hobbs
(74) *Attorney, Agent, or Firm* — Lerner, David, Littenberg, Krumholz & Mentlik, LLP

(57) ABSTRACT

A system and method is provided for non-invasively measuring changes in a specimen suspected of containing one or more microbes, by monitoring changes in the dielectric constant of the specimen caused by metabolic processes of such microbes.

8 Claims, 7 Drawing Sheets

(56) References Cited

U.S. PATENT DOCUMENTS

| | | | |
|---|---|---|---|
| 5,583,432 A * | 12/1996 | Barnes | 324/204 |
| 6,107,924 A * | 8/2000 | Kasai et al. | 340/627 |
| 6,451,978 B2 * | 9/2002 | Winge | 530/380 |
| 2003/0184317 A1 | 10/2003 | Yamagishi et al. | |
| 2004/0009572 A1 | 1/2004 | Felice et al. | |
| 2004/0058453 A1 * | 3/2004 | Free et al. | 436/183 |

FOREIGN PATENT DOCUMENTS

| | | |
|---|---|---|
| JP | 59013948 A | 1/1984 |
| JP | 06201633 A | 7/1994 |
| WO | WO2006071800 | 6/2006 |

OTHER PUBLICATIONS

European Examination Report for Application No. 05855437.9 dated Apr. 24, 2014.

* cited by examiner

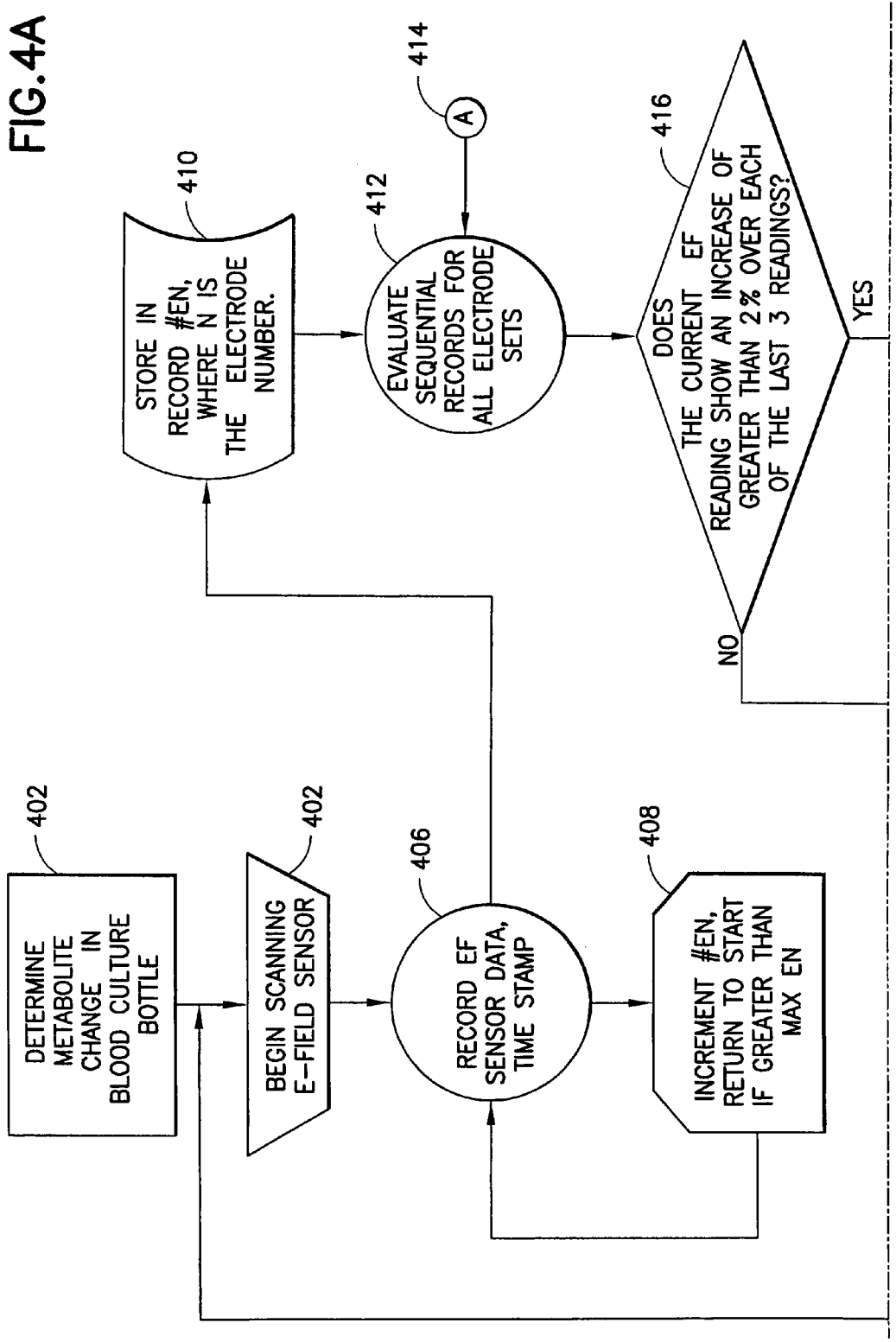

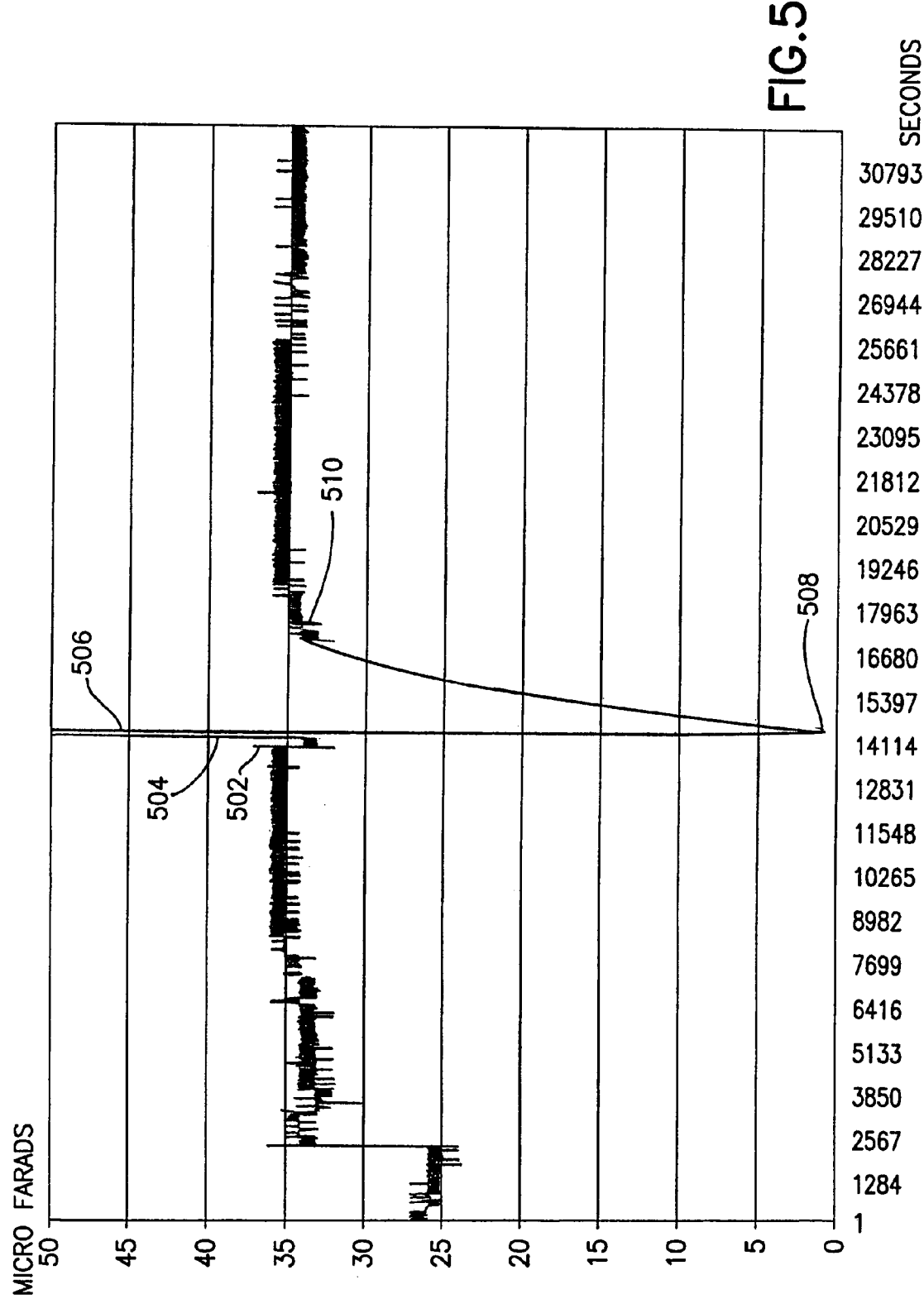

DETECTION METHOD AND APPARATUS FOR DETECTING MICROBIAL GROWTH

RELATED APPLICATION

This application claims priority to U.S. Provisional Patent Application No. 60/639,366 filed Dec. 27, 2004, the disclosure of which is hereby incorporated by reference.

FIELD OF THE INVENTION

The present invention relates to a system and method to measure a change in a biological sample in a non-invasive manner to avoid contamination of the sample.

BACKGROUND OF THE INVENTION

Currently, the presence of biologically active agents such as bacteria in a patient's body fluid, and especially in blood, is determined using blood culture vials. A small quantity of blood is injected through an enclosing rubber septum into a sterile vial containing a culture medium and the vial is then incubated and monitored for bacterial growth.

Common visual inspection of the culture vial then involves monitoring the turbidity or observing eventual color changes of the liquid suspension within the vial. Known instrument methods can also be used to detect changes in the carbon dioxide content of the culture bottles, which is a metabolic byproduct of the bacterial growth. Monitoring the carbon dioxide content can be accomplished by methods well established in the art; however, most of these methods require invasive procedures which can result in the well-known problem of cross-contamination within the vial.

One solution to the above problems includes the use of a non-invasive infrared microorganism detection instrument in which special vials having infrared-transmitting windows are utilized. These vials, however, are relatively expensive. In yet another solution, glass vials are transferred to an infrared spectrometer by an automated manipulator arm and measured through the glass vial. The disadvantage of this system is that, due to the high infrared absorption of glass, small changes in the glass wall thickness can generate large errors in the measured headspace gas absorption. These problems can be partly reduced by utilizing high-quality glass vials, but this measure results in relatively high vial cost.

Still other solutions have included the use of chemical sensors disposed inside the vial. These sensors respond to changes in the carbon dioxide concentration in the liquid phase by changing their color or by changing their fluorescence intensity. These techniques are based on light intensity measurements and require spectral filtering in the excitation and/or emission signals. However, in such solutions, errors can occur if any of the light source, photodetector, filters, or sensor show aging effects over time, which would vary the intensity response.

Accordingly, a need exists for a system and method to measure a change in a sample in a non-invasive manner to avoid contamination of the sample.

SUMMARY OF THE INVENTION

In one embodiment, the invention provides a system and method to measure the changes in the dielectric constant of a biological sample in a growth medium as microbes metabolize the essential components of the medium into metabolic byproducts.

In another embodiment, the invention provides a system and method for establishing an electrodynamic field such that minute changes to a biological sample's dielectric constant through the destruction and formation of various organic and inorganic compounds will change a capacitance value. (As used herein, electrodynamic field indicates an electric field set up such that physical or chemical changes induce measurable electrical changes, e.g., a varying electric field capable of sensing a change in dielectric constant between capacitive electrodes).

In a further embodiment, the invention provides a system and method for measuring a change in capacitance value and determining a corresponding change value for a biological growth material.

According to an embodiment, a system and method is provided for generating an electrodynamic field on at least one and preferably a plurality of electrodes, positioned adjacent to a sample, and which have a suitable self-capacitance to virtual ground such that minute capacitance changes within the sample can be measured. The electrodes are not required to be placed in direct contact with the sample, as changes to the sample's dielectric constant through the destruction and formation of various organic and inorganic compounds will change the capacitance of the electrodes to virtual ground, and provide a measurement corresponding to the sample changes occurring.

BRIEF DESCRIPTION OF THE DRAWINGS

The above and other objects and advantages will be apparent upon consideration of the following drawings and detailed description. Embodiments of the present invention are illustrated in the appended drawings, in which:

FIG. 5 is a graph illustrating an example of the capacitance change detectable using a non-invasive dielectric sensing apparatus in accordance with an embodiment of the present invention;

In the drawing figures, it will be understood that like numerals refer to like elements.

DETAILED DESCRIPTION

One embodiment of the invention, an electrodynamic field is generated using at least one, and preferably a plurality of electrodes which are positioned adjacent to a sample containing a biological sample that may include microbes such as bacteria, typically in a growth media, the electrodes having a suitable self-capacitance to virtual ground such that minute changes can be measured. The electrodes are not required to be placed in direct contact with the sample, as changes to the sample's dielectric constant through the destruction and formation of various organic and inorganic compounds will change the capacitance of the electrodes to virtual ground. Typically, the entirety of the sample's dielectric constant is measured, but it is possible to set up electrodes to monitor portions of the sample, e.g., a circumferential portion. While fluid samples in a growth media are typical, solid samples such as food products or tissues are also contemplated.

Figure 1:
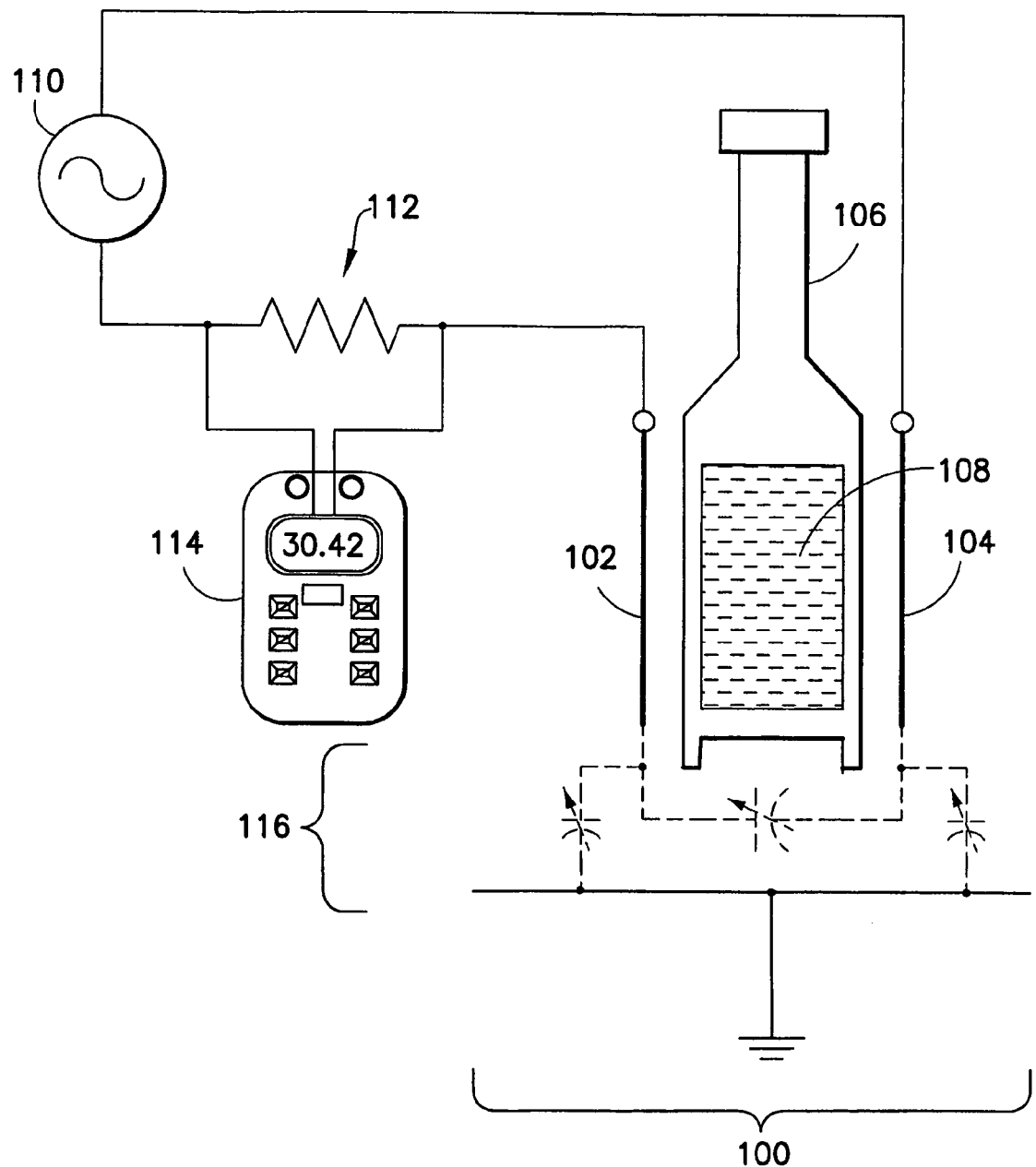
FIG. 1 is a schematic diagram of an embodiment of the invention.

In an embodiment of the invention shown schematically in FIG. 1, a circuit 100 comprising two conductive electrodes 102 and 104 is placed around the circumference of an insulative growth vessel or bottle 106. In one aspect, the electrodes 102, 104 are configured in an interdigitated format, as more clearly shown in FIG. 2A. Electrode 102 can be configured as a sensor electrode, and electrode 104 can be configured as a ground reference electrode. The flexible circuit 100 is typically wrapped around the vessel or bottle 106, such that an electrode surface area is in physical proximity to the liquid sample 108 inside, where the dielectric constant of the sample 108 changes with microorganism growth and metabolite release.

The conductive sheets of both electrodes 102 and 104 are connected to a differential alternating current signal generator 110 which produces a sine wave to quantify circuit impedance. In the apparatus of FIG. 1, the signal applied to one electrode is 180 degrees out of phase with the signal applied to the other electrode. The frequency of the signal is chosen to provide a current from one electrode to the other through their intercapacitance that can be easily quantified by standard methods as known to those skilled in the art.

A resistor 112 is electrically coupled in series between the signal generator 110 and the sensor electrode 102, wherein the current varies through the resistor 112 at a rate which is inversely proportional to the capacitance between electrodes 102 and 104. A test device 114, such as a digital multimeter (DMM), can then be used to measure the voltage value across the resistor 112.

As noted above, the current varies through the resistor 112 inversely proportional to the capacitance between electrodes 102 and 104. The capacitance between electrodes 102 and 104 can be illustrated by a model circuit 116, which illustrates the variables in free space capacitance between electrodes 102 and 104, between electrode 104 and ground, and between electrode 102 and ground. As known to those skilled in the art, capacitance varies between electrodes and other objects depending on their size, spacing and dielectric properties of the intervening materials (i.e., bottle 106 and the sample 108 inside).

Figure 2A:
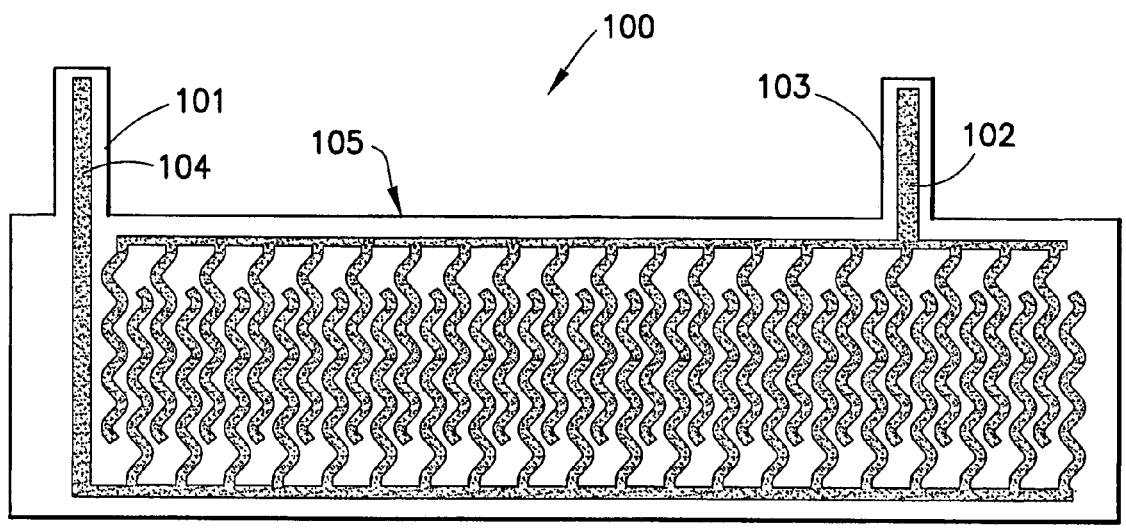
FIGS. 2A and 2B illustrate a flexible circuit in accordance with an embodiment of the invention.
Figure 2B:
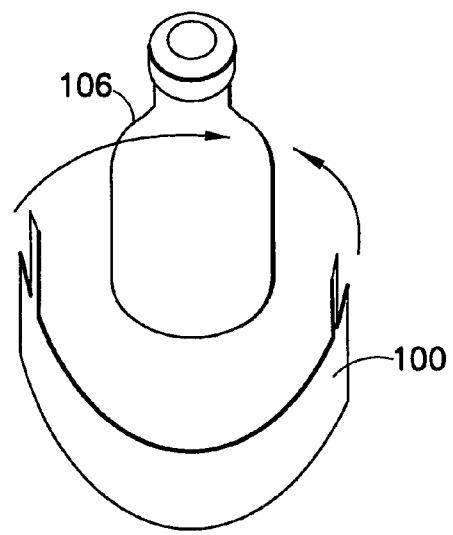

FIG. 2A shows a configuration of the electrodes according to an embodiment of the invention. In FIG. 2A, the interdigitated electrodes 102 and 104 are provided on or in a flexible circuit substrate 105, such as mylar or kevlar film. In some embodiments, the electrodes 102 and 104 are provided with contact tabs 101 and 103 to provide a means to electrically couple each electrode with the signal generator 110. Any number of gaps or spacing can be provided between electrodes 102 and 104 to establish a desired capacitance value. The flexible substrate 105 can then be used to encircle the culture vial or bottle 106 as shown by FIG. 2B. Once encircled, an electromagnetic field is established as apparent to one skilled in the art.

As the dielectric constant of the sample 108 inside the bottle 106 changes, the current between the electrodes 102 and 104 changes in a manner that is inversely proportional to the dielectric constant change of the sample bottle. This is a result of the change in capacitive reactance at the selected frequency. The dielectric constant changes for example, when microorganisms within the sample 108 metabolize sugars into dissolved gases, enzymes, proteins, and waste products. Any number of possible variables effecting the measurements can be evaluated, and these are presented as examples only.

Figure 3:
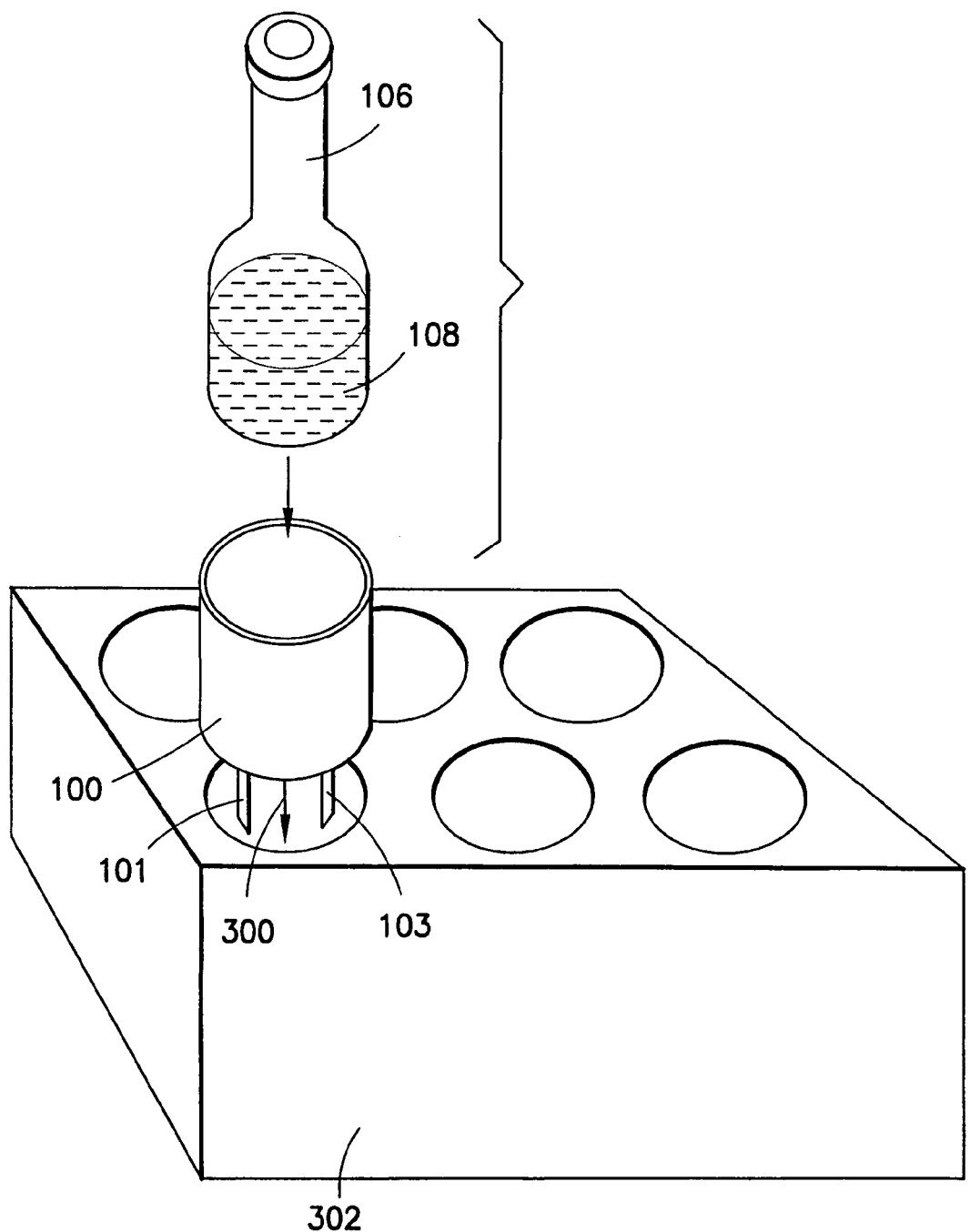
FIG. 3 is a non-invasive dielectric sensing apparatus in accordance with an embodiment of the invention.

FIG. 3 shows an embodiment of a system where multiple bottles 106 can be inserted in an incubator assembly 302 (for convenience only a single bottle 106 is shown). According to this embodiment, each bottle 108 is encircled by the flexible substrate and electrode of a flexible circuit 100, e.g., of the type as described above. The encircled vials 106 can then be fit within each incubator well 300 of the incubator assembly 302. Within each well 300, electrical connectors can be provided (not shown) to receive the contact tabs 101 and 103 of each electrode 102 and 104 disposed upon the flexible substrate of the flexible circuit 100. Once positioned, a method to measure changes in the sample, such as a change in the dielectric constant of a biological growth medium, can be implemented as described herein.

Figures 4, 4B:
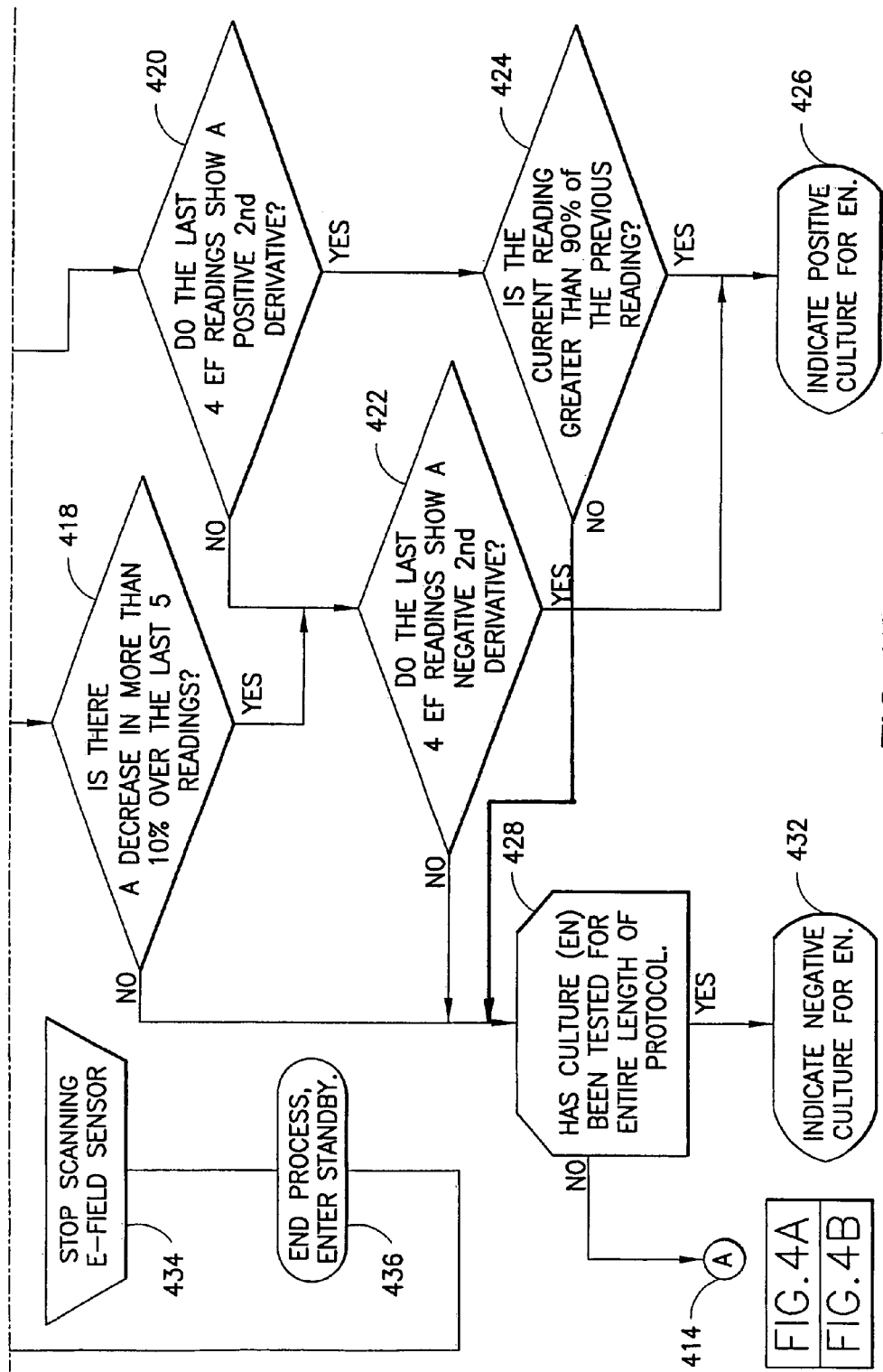
FIG. 4 is a flowchart for a dielectric sensing method in accordance with an embodiment of the invention.

An embodiment of the method of the invention is illustrated in the flow chart of FIG. 4. Specifically, once each bottle 106 is provided with a flexible circuit 100 and positioned within an incubator assembly 302, a user request can be made for detecting changes therein which can be achieved in the following steps 402 through 436. Upon a request to determine a metabolite change in a bottle 106 at step 402, the embodiment of the present invention begins scanning the electrodynamic field (e-field) sensor set (e.g., electrodes 102 and 104) at step 404. (In FIG. 4, "EF" refers to electric field reading and "En" refers to electrode set number—one set per bottle). At this time, the system then records the e-field sensor set data ($EF_1$) of a first bottle, and time stamps the measurement at step 406. Thereafter, at step 408 the system moves to the next e-field sensor set—En, records the e-field sensor set data, and time stamps the measurement. The system continues to repeat steps 406 and 408 until each set of e-field sensors has been measured and recorded, and then returns to start when e-field sensors of all the bottles 106 have been measured.

Once a complete pass of all sensor sets has been completed in steps 406 and 408, the system then stores the measurements in a record for the specific sensor sets, respectively, at step 410. At step 412, the system can then evaluate sequential records for each sensor set. At step 416, the system can then detect changes in measured values, such as in this example, detecting if the current electric field reading shows an increase of greater than 2% over each of the last three readings. If not, the system evaluates the information at step 418 to determine if there is a decrease in the electric field reading of more than 10% over the last five readings. If there is an increase at step 416, the system then determines if the last four electric field readings show a positive second derivative at step 420.

If the readings do not show a positive second derivative at step 420, then the system evaluates the information at step 422 to determine if the last four electric field readings show a negative second derivative. If there is a positive second derivative at step 420, the system then determines at step 424 if the increase in the current reading is greater than 90% of the value of the previous reading. If the increase of the current reading is greater than 90% of the value of the previous reading at step 424, the system then determines that there is an indication of positive culture for the electrode at step 426. In other words, if the value of the current reading shows a value of signal strength at least 90% or higher of the previous reading, a "positive" is declared. If the reading tested in step 424 is less than 90% of the previous reading, the system proceeds to step 428 to determine if the culture of the electrode being scanned has been tested for the minimum period as established by the test protocol. If the test protocol period is satisfied, the system determines an indication of negative culture at steep 432. If the test protocol period has not been satisfied the system resumes scanning at 402.

Returning to step 418, if there is a decrease in the electric field reading of more than 10% over the last five readings at step 418, the system proceeds to step 422. If not, the system evaluates the information at step 428 to determine if the culture of the electrode has been tested for a minimum period as established by protocol. If the period is satisfactory, the system determines that there is an indication of negative culture for the electrode at step 432. In other words, if the value of the current reading shows no drop in signal strength from the previous reading, a "negative" is declared. A lack of drop in the dielectric constant of the culture bottle's liquid contents can indicate no metabolic process change has occurred. If the period is not satisfactory, the system returns to step 412.

Returning to step 422, if the last four electric field readings show a negative second derivative at step 422, the system proceeds to step 426. A sudden precipitous drop in the dielectric constant of the culture bottle's liquid contents can indicate a metabolic process change by any microorganism present. For instance, the conversion from glucose metabolism to catabolism. If not, the system then proceeds to step 428. Upon completion, of all sensor scanning for the entire length of each culture's protocol, the system stops scanning the e-field sensors at step 434, and enters a standby mode at step 436.

Variations in the above process are of course possible, depending on, for example, the parameters of the particular system or the particular sample type.

Example

A BD BACTEC™ Plus Aerobic/F culture bottle was obtained. A single, flexible electrode of the type shown in FIG. 2A was assembled. Tin-coated copper adhesive tape was pre-cut to form the interdigitated fingers and placed on a 0.005 inch thick Mylar substrate. Electrical connections to the two electrodes were formed by two tabs extending from the fingers, and were connected to an electrical circuit board. The electrode was placed onto the bottle, to circumferentially surround it.

The electrode was attached to a Motorola 33794 Electric Field Imaging Device evaluation module, which is a device designed for sensing objects within its self-generating electric field. Data was logged by a personal computer running a LabView "virtual instrument" application specifically designed for the 33794 device. The program periodically sent a digital signal to the 33794 via a serial data connection, and the integrated circuit of the 33794 would measure the amount of field in the electrode, and send it to the computer for storage. The plot of FIG. 5 is a representation of that data. FIG. 5 shows the change in capacitance in the bottle based on *E. coli* growth, having a vertical axis indicating measured capacitance in microfarads, and a horizontal axis indicating time in seconds. At point 502, an inoculation of 0.1 ml of *E. coli* was made into the bottle. At point 504, approximately 26 minutes later, a rise is shown in the capacitance measured by the electrodes. The saturation ends approximately 55 seconds later at point 506, marked by a decrease in the measured capacitance to a value at point 508. The capacitance returns to an equilibrium point 510 approximately 4 hours later. These minute capacitance changes within the sample are measured via the electrodes and provide a measurement corresponding to the sample changes occurring.

Figure 6:
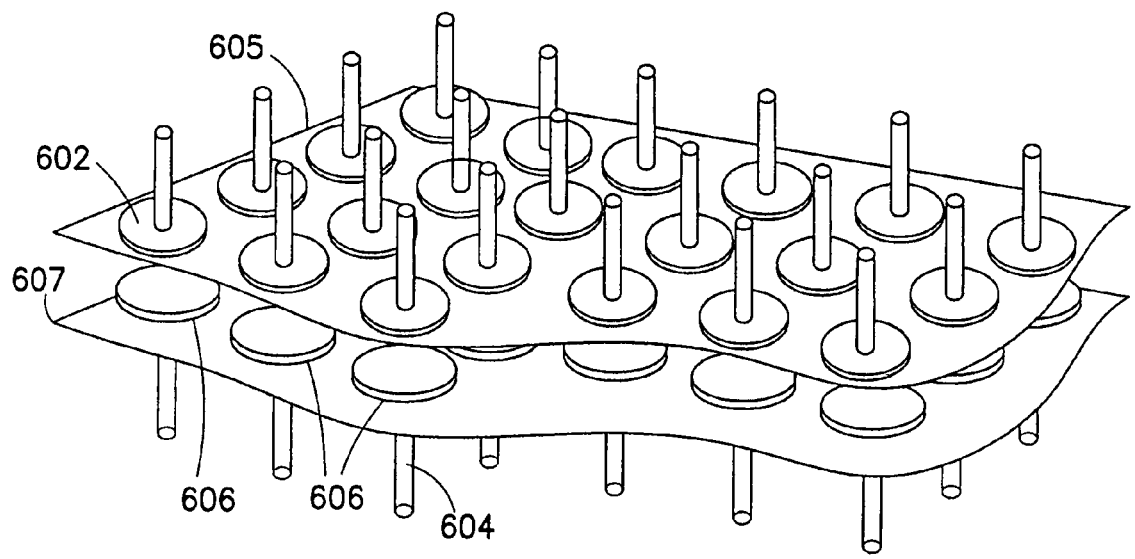
FIG. 6 illustrates another embodiment of the invention.

In addition to the bottles shown above, other containers can be used according to embodiments of the invention. In the embodiment of FIG. 6, plates 605 and 607 include opposing pairs of conductive electrodes 602 and 604, wherein each pair of electrodes are placed above and below microtiter wells 606. Electrode 602 can be configured as a sensor electrode, and electrode 604 can be configured as a ground reference electrode, substantially as described above in FIG. 1. The plates 605 and 607 are positioned such that an electrode surface area is in physical proximity to the microtiter wells 606, wherein the dielectric constant of the microtiter wells 606 change with microorganism growth and metabolite release of samples located in the wells. The remaining functions and implementation of the electrodes 602 and 604, are substantially the same as those described above.

Figure 7:
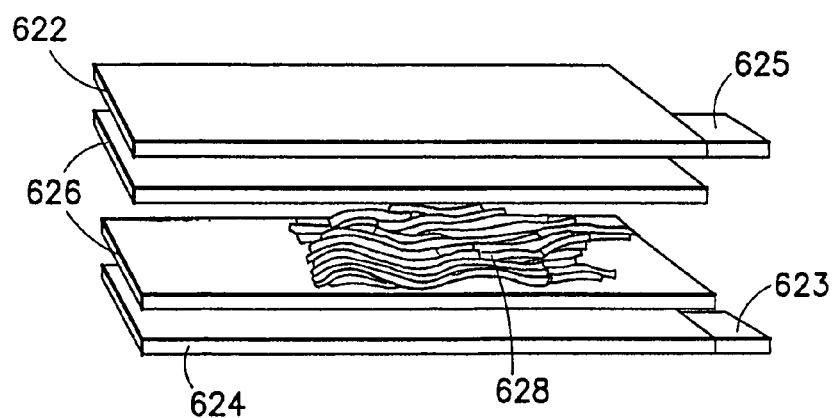
FIG. 7 illustrates a further embodiment of the present invention.

An embodiment of the invention useful with viscous or solid samples, such as food or tissue, is shown in FIG. 7. According to this embodiment, the container consists of disposable compression plates 626 to surround a sample 628. Electrode plates 622 and 624 can be provided as shown, having tabs 623 and 625, respectively. Conductive electrode plates 622 and 624 are placed above and below sample compression plates 626. Electrode 622 can be configured as a sensor electrode, and electrode 624 can be configured as a ground reference electrode in a configuration such as shown in FIG. 1. The electrodes and plates are positioned such that an electrode surface area is close enough to the sample 628 to allow measurement of the dielectric constant of the sample 628 as it changes with microorganism growth and metabolite release. The remaining functions and implementation of the embodiment of FIG. 7, are substantially the same as those described above.

Embodiments of the present invention can solve problems associated with varying media fill density, varying vial geometry, container material transparency, mixture of solid, liquid, and semisolid components in the container contents, and differences in the container material, whether plastic or glass. The design of the interrogating electrodes can be further used to determine the sensitivity and selectivity of the sensor to different components of the system.

The use of an electrodynamic field substantially avoids measurement problems associated with variations in bottle sources, media types, resin fills, and artifact effects (foam, magnetic stirring element, settling, etc.). For example, effects such as foaming, presence or absence of stirring element, blood settling, and presence/absence of blood in the culture vessel generally do not affect measurements based on changes in the electrodynamic field. Similarly, the container, vessel, vial or bottle bottom does not need to be perfectly flat or indented as shown in FIG. 1.

Embodiments of the present invention can be applied to a variety of biological sensing applications, such as infectious disease/antibiotic susceptibility testing, or the identification and antimicrobial sensitivity testing of particular microbiological isolates. Another application is the detection of contaminating organisms on food products and pharmaceuticals.

Embodiments of the present invention can further be applied to the sensing of inorganic or organic chemical reactions that result in the formation of compounds that have a measurably different dielectric constant than the original reactants. Variable initial permittivity that is experienced in different media types due to their varying chemical composition generally requires foreknowledge of the medium type to apply the correct interpretive algorithm.

Also, embodiments of the invention can be used to detect volume levels in a container, as well as degree of agitation. For example, the fill volume can be estimated to within 1 ml for a 60 ml container (<2% error). Thus, uses beyond growth detection are possible.

The invention is believed to be superior to other methods which detect the growth of microbes because of a substantially increased sensitivity. For example, it has been shown that recovery of growth following microbial stress can be detected within one hour for *E. coli* and *S. epidermitis* with the present invention.

In addition to the reduction in time to detect growth, it is believed the invention is capable of detecting much lower concentrations of organisms than current methods. An additional advantage provided by the embodiments of the present invention is that the measurements can be taken from outside the bottle electrically, and hence the container need not be optically transparent.

Although only certain exemplary embodiments of the present invention have been described in detail above, those skilled in the art will readily appreciate that many modifications are possible in the exemplary embodiments without materially departing from the novel teachings and advantages of the present invention. Accordingly, all such modifications are intended to be included within the scope of this invention as defined in the appended claims and equivalents thereof.

What is claimed is:

1. A system for determining the presence or absence of microbes in a specimen, said system comprising:
   a sealed blood culture bottle for holding a specimen comprising a growth media; and
   a circuit comprising:
      at least two electrodes, the electrodes located in contact with or in proximity to the bottle such that the at least two electrodes are adjacent to, but not in contact with, the specimen upon collection thereof, wherein the bottle is cylindrical or comprises a cylindrical portion and wherein the at least two electrodes are disposed circumferentially around the bottle, and wherein the at least two electrodes are interdigitated, and wherein the first of the two interdigitated conductive electrodes is a sensor electrode and a second of the two interdigitated conductive electrodes is a ground reference electrode;
   a signal generator that generates a signal with a frequency selected to provide current from the sensor electrode to the ground reference electrode through an intercapacitance between the sensor electrode and the ground reference electrode, such that an electrodynamic field forms over at least a portion of the specimen; and
   a test device capable of measuring a value of the electrodynamic field, wherein the value is capacitance which is indicative of the dielectric constant of the specimen, and wherein a measured change in capacitance is indicative of changes in the specimen caused by metabolic processes of the microbes contained therein.

2. The system of claim 1, wherein the interdigitated sensor and ground reference electrodes are disposed in a substantially planar circuit that is wrapped around the bottle.

3. The system of claim 2, wherein the signal generator is connected with the sensor electrode and the ground reference electrode, wherein the signal generator produces a sine wave, and wherein the signal applied to the sensor electrode is 180° out of phase with the signal applied to the ground reference electrode.

4. The system of claim 2, wherein the interdigitated sensor and ground reference electrodes are disposed on an insulative, flexible substrate.

5. The system of claim 1, further comprising a plurality of the bottles and an incubator assembly comprising one or more incubator wells for receiving the bottles and at least a portion of the at least two electrodes, wherein the incubator wells comprise electrical connections for the at least two electrodes.

6. The system of claim 1, wherein the bottle comprises the specimen, and wherein the specimen is a biological specimen suspected of containing one or more microbes.

7. A system for determining the presence or absence of microbes in a specimen, said system comprising:
   a sealed blood culture bottle for holding a specimen comprising a growth media; and
   a circuit comprising:
   at least two electrodes located in contact with or in proximity to the bottle such that the at least two electrodes are adjacent to, but not in contact with, the specimen upon collection thereof, wherein the bottle is cylindrical or comprises a cylindrical portion and wherein the at least two electrodes are disposed circumferentially around the bottle, and wherein the at least two electrodes are interdigitated, and wherein the first of the two interdigitated conductive electrodes is a sensor electrode and the second of the two interdigitated conductive electrodes is a ground reference electrode;
   a signal generator for directing current through the at least one electrode at single frequency, such that an electrodynamic field forms over at least a portion of the specimen; and
   a test device capable of measuring a value of the electrodynamic field, which is indicative of the dielectric constant of the specimen, and wherein a measured change in the dielectric constant over time is indicative of changes in the specimen caused by metabolic processes of the microbes contained therein,
   wherein the at least two electrodes are disposed on an insulative, flexible substrate.

8. The system of claim 1, wherein the bottle is optically non-transparent.

* * * * *